United States Patent [19]

Rimer

[11] Patent Number: 5,347,860
[45] Date of Patent: Sep. 20, 1994

[54] BENTHIC SAMPLING EFFECTIVENESS MEASURER

[76] Inventor: J. Patton Rimer, 960 W. 19th St., Upland, Calif. 91786

[21] Appl. No.: 124,864

[22] Filed: Sep. 21, 1993

[51] Int. Cl.$^5$ .................. A01K 73/02; G01N 1/00
[52] U.S. Cl. ..................... 73/170.33; 43/9.1; 73/170.32
[58] Field of Search ........... 73/170.33, 170.29, 170.32, 73/863.23; 43/9.2, 100, 9.1

[56] References Cited

U.S. PATENT DOCUMENTS

| | | | |
|---|---|---|---|
| 3,482,034 | 12/1969 | Rhoades et al. | 73/170.33 |
| 3,501,953 | 3/1970 | Cudlitz et al. | 73/170.33 |
| 4,554,759 | 11/1985 | Edling et al. | 43/100 |
| 5,123,195 | 6/1992 | Hawkins | 43/9.2 |

*Primary Examiner*—Donald Woodiel
*Attorney, Agent, or Firm*—Leo R. Carroll

[57] ABSTRACT

This invention provides a device and method for measurement of the actual on-bottom time of a sampling otter trawl used for benthic sampling. The device uses passive measurement of the actual on-bottom time without cables and wires connected to the ship, and is small enough to be mounted on a standard otter trawl door without affecting its net-towing function. The apparatus consists of a sealed bottom contacting and counting sensor which totalizes and displays the accumulated on-bottom time. Power is supplied from a self-contained battery which may be automatically recharged by a solar cell. In operation, a flexible trigger arm is mounted so as to extend below the runner on the bottom edge of the trawl door. When bottom contact is first made, the trigger arm bends and mechanically causes a magnet to move sufficiently close to actuate a magnetic switch inside a transparent electronic data module. An electronic counter inside the module will count minutes and seconds as long as the magnetic switch is closed. Whenever the spring loaded trigger arm lifts off the bottom, the counter will stop. Actual elapsed bottom time may be read from a liquid crystal display (LCD) through the transparent case after a run. The counter may be reset to zero prior to the next trawl by waving a magnet across the module face, or the time may be allowed to accumulate. The unit has been built and experimentally tested in Southern California waters, during which it was found that the device is very useful for trouble shooting and for making adjustments for weather conditions, bottom currents, trawling direction and scope length. Also, when the net fouls or picks up large debris, intelligent decisions may be made as to whether the trawl bottom time has been impacted.

20 Claims, 6 Drawing Sheets

BENTHIC SAMPLING EFFECTIVENESS MEASURER

BACKGROUND OF THE INVENTION

1. Technical Field

This invention relates generally to the field of ocean bottom environmental monitoring and particularly to equipments useful for determination of the amount of time that an underwater life catching trawl is actually dragged along the bottom.

Agencies responsible for regulation of ocean pollution require and rely on benthic (ocean bottom) trawls for fish and invertebrate samples in order to determine changes in population of local bottom species which might result from growing toxic ocean contamination. Many private and governmental policy decisions relating to ocean dumping, industrial pollution, and sewage disposal are based in part on the results of these bottom trawls. Inaccuracies of the basic data can at best lead to expensive retesting and at worst to flawed policy decisions. Are major problem associated with current benthic trawling is that of obtaining a reliable estimate of the amount of time that the net is actually in contact with the bottom, as opposed to "flying" above the bottom population. For example, if 50 purple sea urchins are collected in a particular location as compared with 100 during a previous quarterly sampling, it is necessary to determine whether the boards were flying half of the time or whether a possible toxic disaster is in the making.

2. Background Art

Typical sample tests require that a trawl net, having a 7.62 meter frontal opening mouth, be pulled along the ocean bottom at a speed between 2 and 2.5 knots for ten minutes. The distance supposedly covered along the bottom is about 770 m. The net mouth opening is vertically maintained by means of a metal chain weighted footrope and a headrope with floats sewn into the upper edge. Each side of the net is attached to a door, known as an "Otter Trawl Door", which is dragged upright on a runnered edge along the bottom. The function of the doors is to pull the trawl net down and to maintain the mouth of the net open to its regular swath. The doors are also attached to the tow cable which is connected to the trawling vessel by means of a four part chain bridle. The total catch from a trawl in each designated area is brought aboard the vessel, segregated by species and counted.

Benthic sampling is generally done with moderately sized vessels of 13 to 45 meters overall length, equipped with a deck winch and cable drum. Handling and shooting (putting overboard) of the trawl net assembly is done manually. When the trawl net is in the water and tracking smoothly, the towing cable is gradually let out to the desired length. The typical scope (length) of wire cable let out will be three to five times the water depth in the trawl area, which may run from 20 to 1000 meters. Most trawls in the Southern California area are made at depths between 20 to 150 meters.

Most trawl methods include making estimates of the bottom trawl time based upon measured total trawl time, length of tow wire payed out, and floor depth knowledge or measurement. Trawl duration is measured from the time that the winch stops deploying the trawl to the time that the winch starts retrieval. Distance travelled by the boat is measured with LORAN C or a comparable instrument, but it is not a reliable measure of on-bottom time.

The behavior of a particular trawl at a given station can vary substantially from the nominal expected performance because of wind, swell and wave effects on the towing vessel, descent and ascent rate variations of a particular board and net rigging, and current velocity changes down the entire water column.

The type of trawl board described above is illustrated in U.S. Pat. No. 3,299,560 to Luketa for Sectional Trawl Doors. There, each door comprises a door body having separate top and bottom edge sections, the latter of which ride upon the bottom, and an intermediate section. The sectional design is symmetric and either edge may be used downward on either the left or right side.

A variety of other patents have been issued which pertain to either improved trawling devices or to other equipments for environmental benthic monitoring. For example, in U.S. Pat No. 4,771,565, Shepard discloses a Bottom Trawl Roller which can be attached to the net in order to reduce the friction generated as a trawl net is dragged along the bottom during shrimp fishing. Another roller type is disclosed by Holden in U.S. Pat. No. 3,548,531 for a live bait dip net which may also be converted to trawling. Both improvements promote low flying.

U.S. Pat. No. 4,164,199 to Pequegnat discloses a Benthic Aquatic Biotal Monitor for monitoring the chronic impact of pollution, such as industrial and municipal wastes, of aquatic environments upon in situ samples of benthos. The conical enclosure includes a base portion including containers for retaining benthic sample and having permeable walls. A benthic dredge construction is shown in U.S. Pat. No. 3,762,078 in which a dredge is especially adapted for taking samples from the bottom of a body of water. A Submarine Device is described in U.S. Pat. No. 3,415,068 to Casey et al, wherein the apparatus includes a body adapted to be flooded to sink to the bottom of a body of water in order to agitate the bottom and collect benthic specimens.

All of these benthic collectors are relatively static and do not operate at towing speeds that would produce an off-bottom flying problem.

SUMMARY OF THE INVENTION

This invention alleviates the above problems by provision of a separate BENthic Sampling Effectiveness Measurer (herein abbreviated as "BENSEM") device for monitoring the actual on-bottom time of a sampling otter trawl. The apparatus consists of a sealed bottom contacting and counting sensor which totalizes and displays the accumulated on-bottom time. Power is supplied from a self-contained battery which may be automatically recharged by a solar cell. The total unit is small enough to be mounted on a standard otter trawl door without affecting its net-towing function.

In operation, a flexible trigger arm is mounted so as to extend below the runner on the bottom edge of the trawl door. When bottom contact is first made, the trigger arm bends and mechanically causes a magnet to move sufficiently close to actuate a magnetic switch inside a transparent electronic data module. An electronic counter inside the module will count minutes and tenths of minutes as long as the magnetic switch is closed. Whenever the spring loaded trigger arm lifts off the bottom, the counter will stop. Actual elapsed bottom time may be read from a liquid crystal display (LCD) through the transparent case after a run. The counter may be reset to zero prior to the next trawl by waving a magnet across the module face, or the time may be allowed to accumulate.

The unit has been built and experimentally tested in Southern California waters. It has been found that in addition to providing the actual on-bottom time, the device is very useful for trouble shooting and making adjustments for weather conditions, bottom currents, trawling direction and scope length. Also, when the net fouls or picks up large debris, intelligent decisions may be made as to whether the trawl bottom time has been impacted.

It is a prime object of this invention to provide a separate device for measurement of the actual on-bottom time of a sampling bottom trawl.

It is a further object of this invention to provide a device for passive measurement of the actual on-bottom time without cables and wires connected to the ship.

It is an additional object of this invention to provide a method for measurement of the total on-bottom time which will aid in trouble-shooting a defective trawl run.

It is yet another object of this invention to provide a device for measurement of the actual on-bottom time which will fit upon a standard otter trawl board without interfering with it's normal performance.

It is a further object of this invention to provide a device for measurement of the actual on-bottom time which may be inexpensively manufactured, is structurally rigid and safe, and can be easily adapted to existing trawl boards.

The above and other objects, features and advantages of the present invention will become more apparent from the following description when making reference to the detailed description and to the accompanying sheets of drawings.

DESCRIPTION OF THE PREFERRED EMBODIMENT

Figure 1:
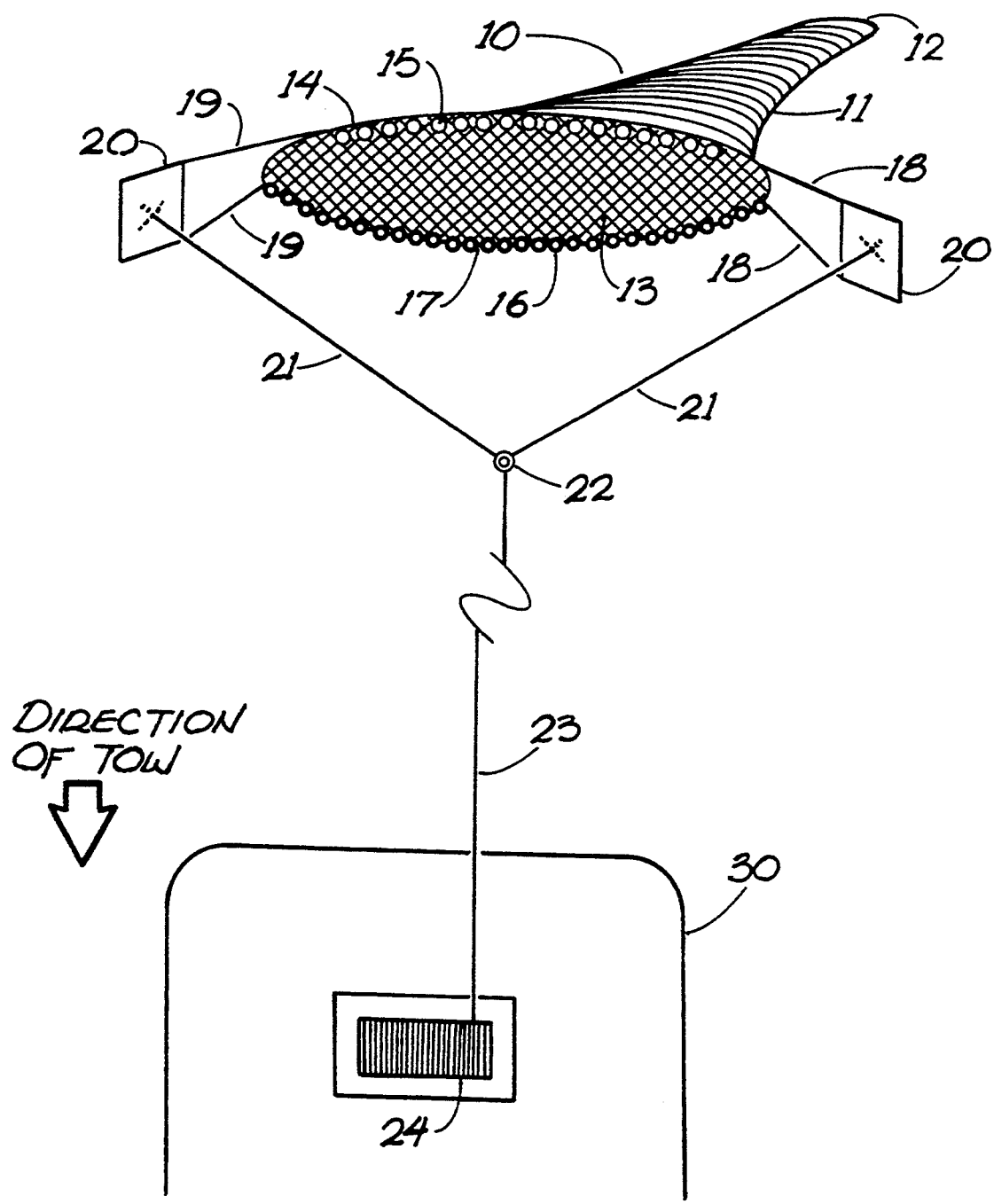
FIG. 1 is an isometric sketch of a standard trawl net with attached otter boards being towed by a trawling vessel.

FIG. 1 presents an isometric sketch of a trawl net assembly 10, attached to otter boards 20, which in turn are rigged for towing by a trawling vessel 30. Net assembly 10 includes net 11 which has a forward facing open oval mouth 13 with a maximum transverse diameter D, said diameter progressively reducing along the longitudinal axis of the net from the forward end to the aft, or "cod" end 12. Mouth 13 is held open in the vertical direction by means of floats 15 attached to a top headrope 14, and by a bottom metal chain 16 which is attached to footrope 16.

Port and starboard otter boards 20 are attached to each side of mouth 13 of net 11 by means of upper and lower leg lines 18, 19. Otter trawl doors 20 are further attached to each other by means of chain bridle 21. Single cable towing is accomplished by cable 23 which connects bridle 21 through swivel 22 placed nears it's midpoint. The forward end of cable 23 is attached to winch 24 mounted on the fantail of towing trawler 30.

Figure 2:
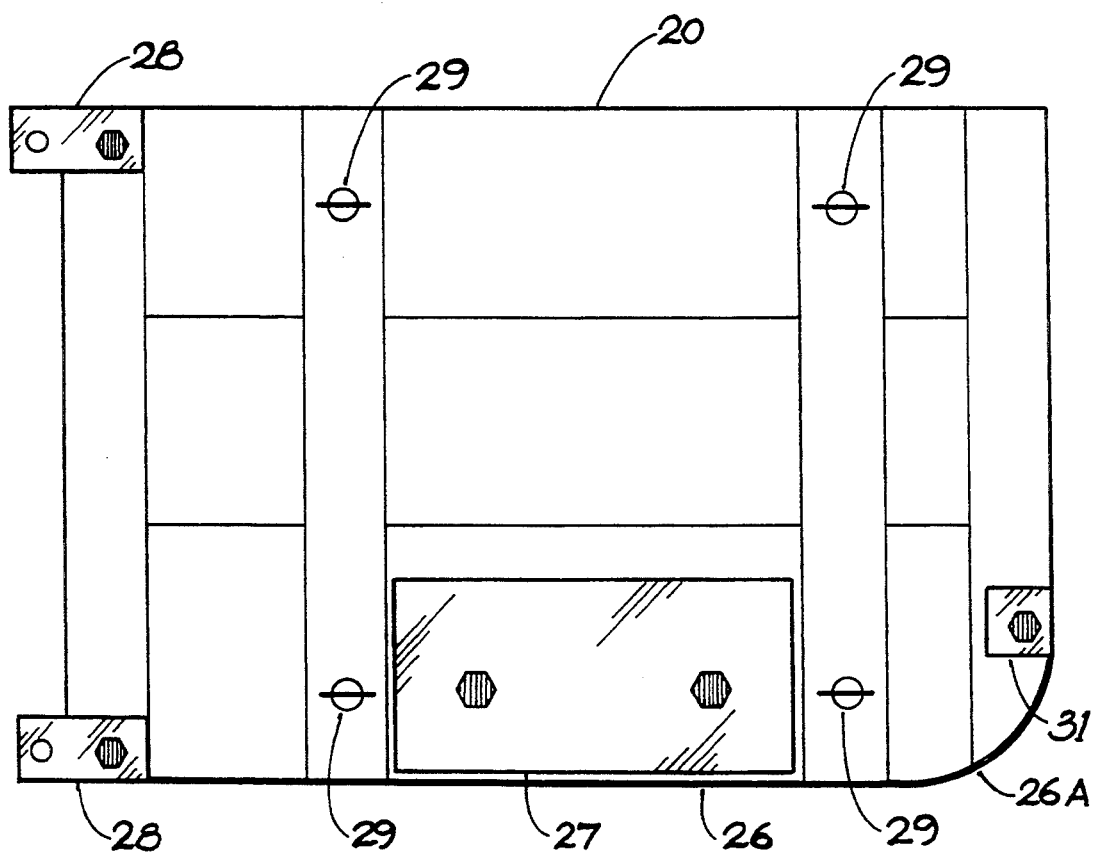
FIG. 2 is a side elevation of the after side of the standard starboard otter trawl board.

A more detailed view of the after side of the starboard otter trawl door 20 is shown in FIG. 2. Bottom edge 26 of door 20 is protected from ocean bottom wear by steel runner plate 26 which covers the entire bottom and bends up in sled-fashion at the forward bottom corner, 26A. Steel runner termination plate 30 secures the front end. Steel ballast plate 27 is placed in the lengthwise middle of the board at the same bottom edge. Upper and lower leglines 19 are attached to the after corners of board 20 through the hole shown in the pair of steel tabs 28. Bars 29 anchor the ends of chain bridle 21, which extend through the holes from the forward side of the door. (not shown) Although other designs are available, the board depicted is that established as a standard for 7.62 meter otter trawls by the Southern California Coastal Water Research Project (SCCWRP).

The size of door 20, is 21" 30" plus the upper and lower legline steel tabs 28. Ballest plate 27 is about 0.5" 6" 12.25", and is made of steel, as are the ¼" 2" runners 26, and the termination plate 31.

Figure 3:
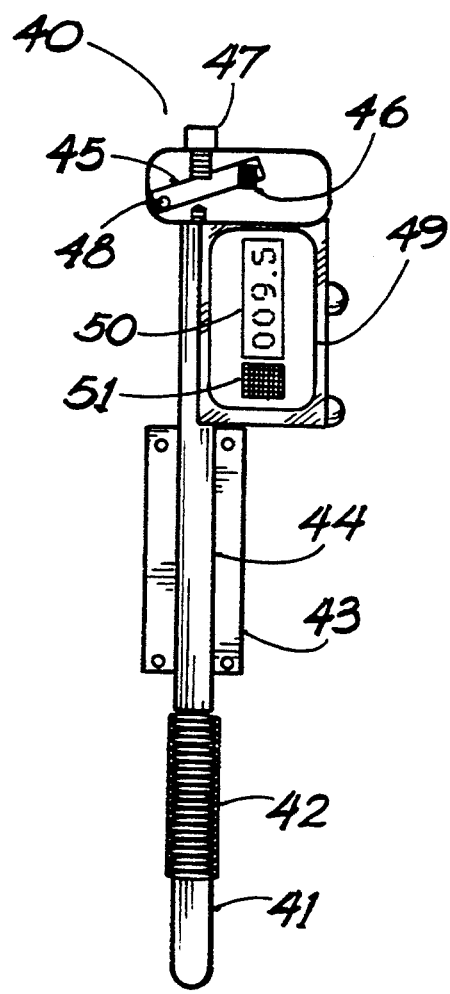
FIG. 3 is a side elevation view of the assembled apparatus of this invention prior to installation.

FIG. 3 shows a side elevation view of the assembled BENSEM apparatus 40 of this invention prior to installation. The device includes bottom contacting trigger arm 41 which is attached to hollow tube 43 by means of spring 42. A centered wire 44 is attached to trigger arm 41 and extends upward through tube 43 to an attachment to arm 45 which is rotatable about pivot 48. Magnet arm 45 is biased upward by spring 47, and supports a small permanent magnet 46 at its end opposite the pivot point. Also mounted at the top end in close proximity to arm 45 is a sealed electronic data module display 49. When trigger arm 41 contacts the ocean bottom, spring 42 is bent away from the direction of trawl. Wire 44 is then extended downward and pulls magnet arm 45 downward which moves magnet 46 toward the upper end of module 49. A magnetic switch is mounted within module 49 at its upper end and will be activated by the motion of magnet 46. Closure of the switch starts counter 50 runner. When trigger arm 41 clears the bottom, arm 45 is pulled upward by spring 47, thereby moving the magnet 46 upward and deactivating the magnetic switch and timer.

Arm 45 is made of a non magnetic material such as aluminum ad other metal parts are stainless steel. Electronic data module display 49 is mounted under a transparent cover to facilitate reading. The display shows as LCD readout of 9.5 minutes of on-bottom time. The blackened square 51 is a solar cell used to recharge an internal battery (not shown).

Figure 4:
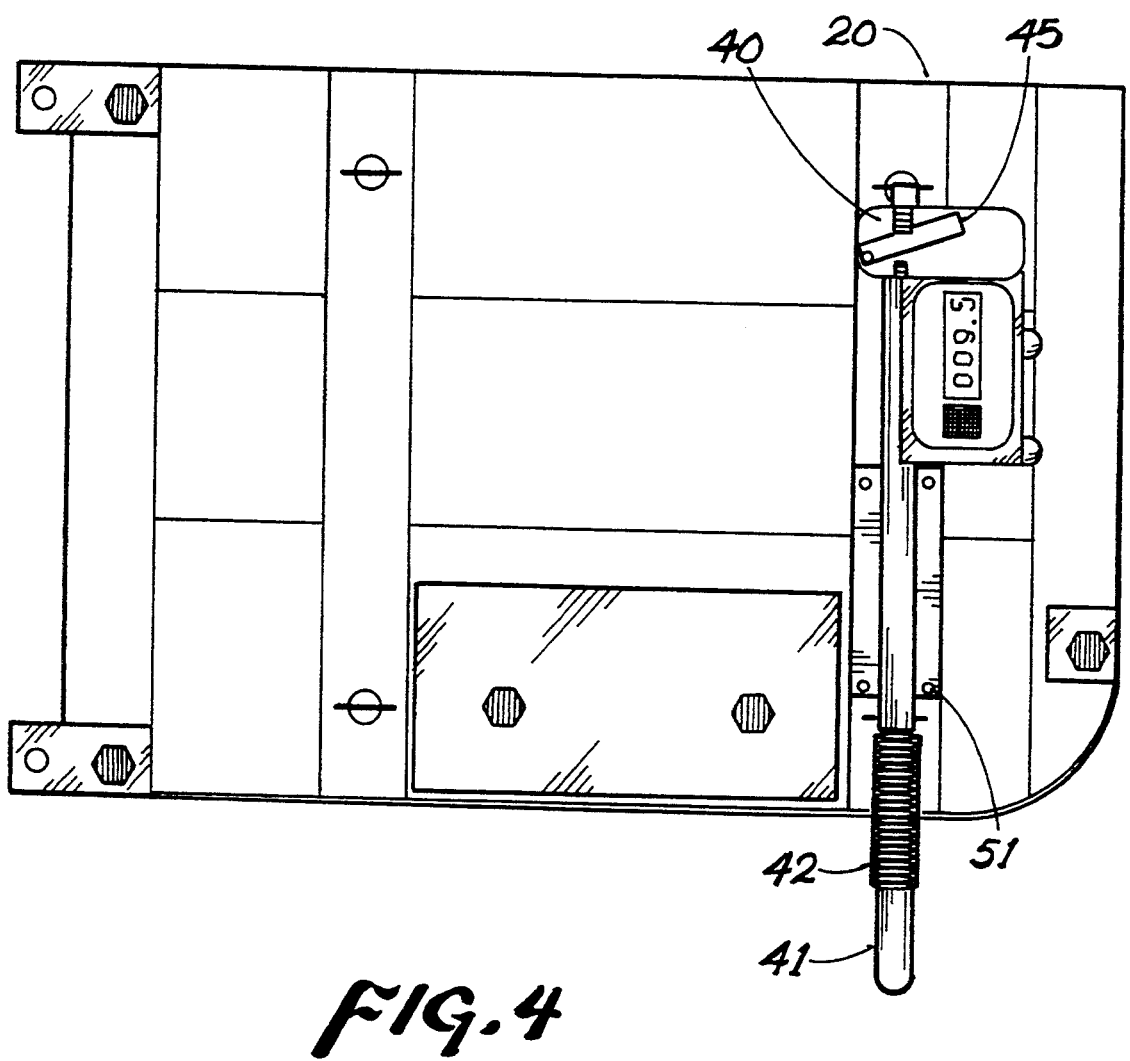
FIG. 4 is a side elevation view of the after side of the starboard otter trawl door with the apparatus of FIG. 3 installed thereon.

FIG. 4 is a side elevation view of the after side of the starboard otter trawl door 20 with apparatus 40 of FIG. 3 installed thereon. The BENSEM unit is mounted on the forward portion of door 20 by means of four bolts 51. The unit is disposed such that the trigger arm 41 and about half of spring 41 extend below the bottom runner just aft of the leading edge 26A of said runner. The data display 49 is again shown as it would appear after a 9.5 minute run.

Figure 5:
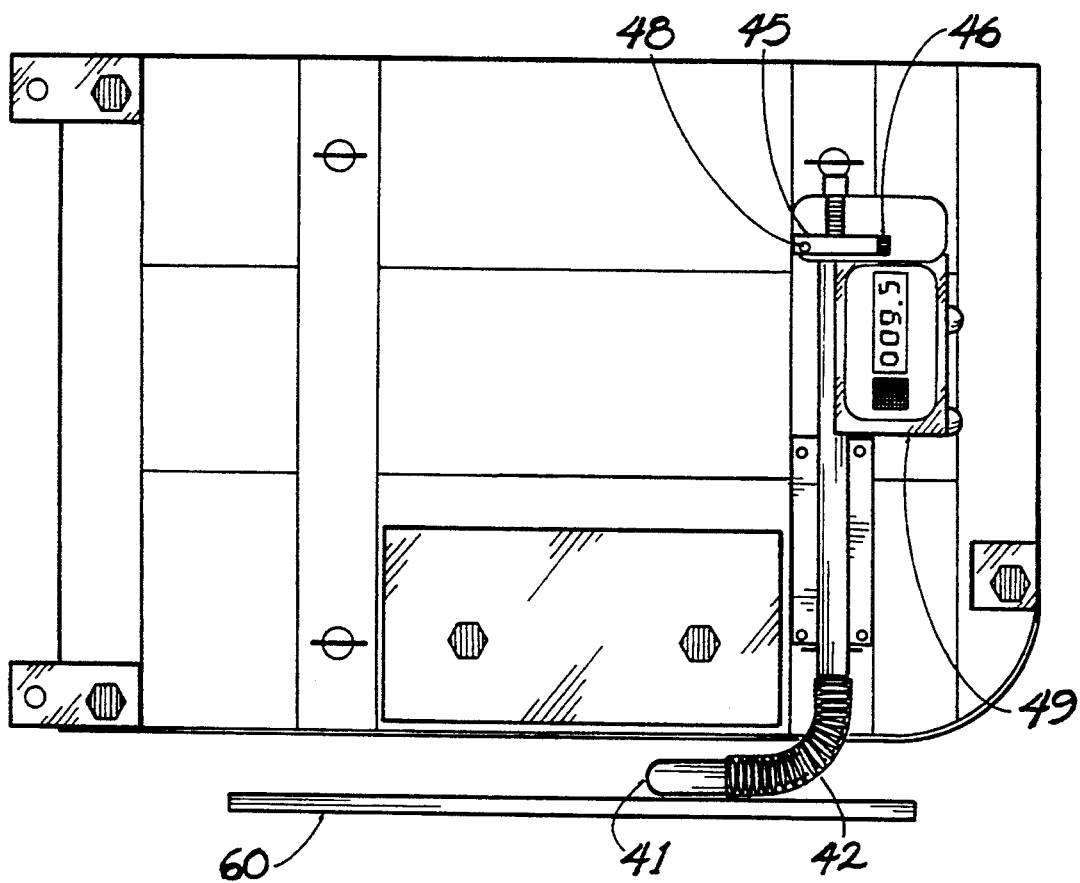
FIG. 5 depicts the side elevation view of FIG. 4 with the trigger arm of this invention in contact with the ocean floor.

FIG. 5 depicts the side elevation view of FIG. 4 with the trigger arm 41 in contact with the ocean floor 60. Aluminum magnet arm 45 has now rotated clockwise about pivot point 48 so as to move magnet 46 next to the upper end of data module 49. In this mode a magnetic switch inside the module will be activated and the timer will be running. A second magnetic switch is also mounted under the cover. When a second permanent magnet is manually waved across the face, the timer will stop.

Figure 6:
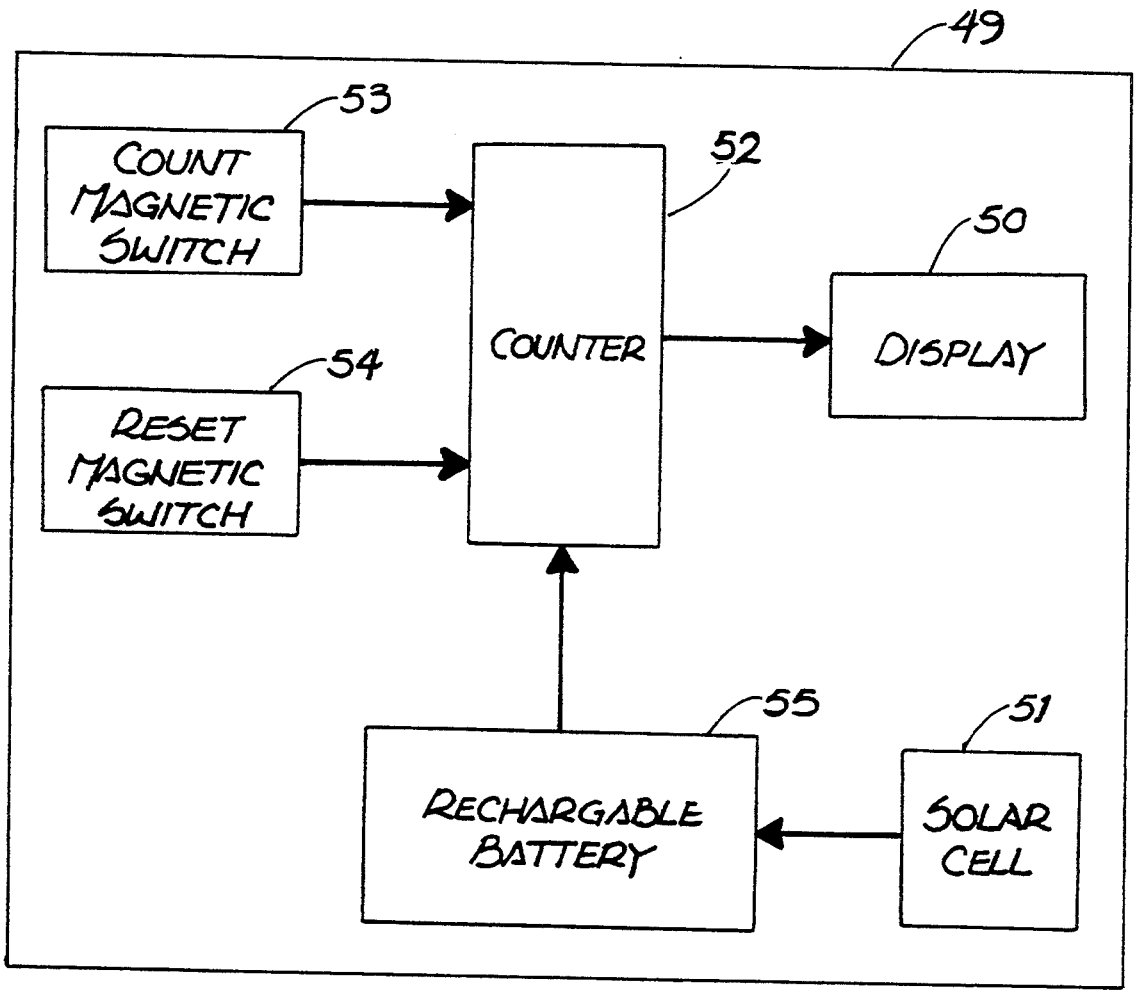
FIG. 6 shows a block diagram of the sealed electronics module contained within this invention.

FIG. 6 shows a block diagram of the sealed electronics data module 49. The unit comprises a pair of magnetic switches 53, 54, a conventional electronic counter module 52, an LCD readout module 50, a rechargeable battery 55, and a solar cell 51 to recharge the battery. Magnetic switch 53 is used to start the counter running, and switch 54 is used to reset to zero.

Figure 7:
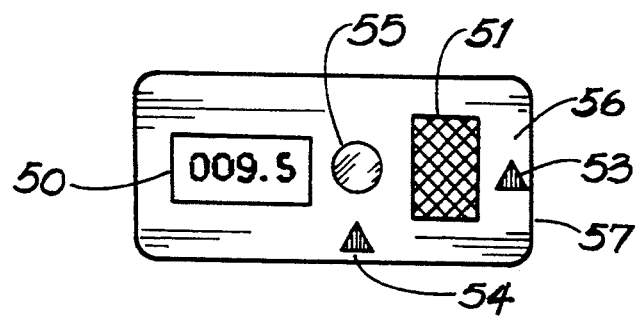
FIG. 7 presents a front face view of the sealed electronics module.

FIG. 7 presents a view of the front face 56 of the sealed electronics module 49. The unit is water sealed within a transparent case 57, with display 50 mounted so as to be easily seen. Counter electronics are powered by a small rechargeable battery similar to those used in digital watches. Solar cell 51 recharges the unit whenever the trawl is exposed to sunlight.

When a trawl is recovered, the display is manually read and recorded on a data sheet. The display unit is then reset to zero by waving a magnet over the face and the unit is ready for the next trawl.

The above configuration was chosen in order to provide a low cost, reliable passive solution to this problem which would not place additional equipment burdens on the ship. It was recognized that many more complex arrangements are possible, including those that might actively or semiactively transpond with depth information when interrogated by shipboard sonar.

The basic concepts of the techniques and apparatus for this simple solution have been illustrated herein and the spirit and scope of the appended claims should not necessarily be limited to those preferred versions.

What is claimed is:

1. An improved water bottom contacting trawl door for towing a trawl net and including a body section having separate top and bottom edge portions, the latter riding upon the water bottom, wherein the improvement comprises:

means for measurement of the cumulative amount of time that said bottom edge portion of said body section is in proximate contact with said water bottom; and means for mounting said time measurement means on said body section.

2. An improved water bottom contacting trawl door as recited in claim 1, in which the means for measurement of the cumulative amount of time that said bottom edge portion of said body section is in proximate contact with said water bottom comprises;

bottom contacting means mounted on said body section and extending below said bottom edge portion of said body section for indication of when said bottom edge portion of said body section is in proximate contact with said water bottom;

time totalizing means for measurement of time cumulation when activated and for holding said time cummulation when deactivated; and first switching means connected between said bottom contacting means and said time totalizing means so that a bottom contacting indication from said bottom contacting means will activate said time totalizing means and that an absence of such indication will deactivate said time totalizing means.

3. An improved water bottom contacting trawl door as recited in claim 2, in which the means for measurement of the cumulative amount of time that said bottom edge portion of said body section is in proximate contact with said water bottom further comprises display means to convert said total time measurement to a visual output.

4. An improved water bottom contacting trawl door as recited in claim 3, further comprising a transparent case for support and observation of said display output.

5. An improved water bottom contacting trawl door as recited in claim 4, is which said transparent case is water sealed.

6. An improved water bottom contacting trawl door as recited in claim 2, wherein said bottom contacting means comprises:

a hollow tube mounted on said body section, having top and bottom ends thereon;

a flexible arm connected to said bottom end of said hollow tube and extending below said bottom edge portion of said body section so that said flexible arm will produce a bending indication when in moving contact with said water bottom; and means for communication of said flexible arm bending indication through said hollow tube to said first switching means so that said bending indication from said bottom contacting means will activate said time totalizing means and that an absence of said indication will deactivate said time totalizing means.

7. An improved water bottom contacting trawl door as recited in claim 6, wherein said flexible arm comprises:

spring means having inboard and outboard ends thereon with the inboard end connected to said bottom end of said hollow tube and the outboard end extending below said bottom edge portion of said body section;

a flexible arm tip connected to said outboard end of said spring means for contacting the bottom; and attachment means for connection of said communication means to said flexible arm tip for transmittal of the flexible arm bending indication through said hollow tube to said first switching means.

8. An improved water bottom contacting trawl door as recited in claim 2, wherein said time totalizing means comprises:

clock counter means for generation of a time count when activated;

second switch means for activation of said clock means when a first magnet is moved toward a first position adjacent said second switch means;

means for deactivating said clock means when said first magnet is moved away from said first position adjacent said second switch means;

third switch means for resetting said time count to zero when a second magnet is moved toward a second position adjacent said third switch means; and power means connected to said counter, display, and switches, for supplying energy for operation of all said elements.

9. An improved water bottom contacting trawl door as recited in claim 8, wherein said first switching means connected between said bottom contacting means and said time totalizing means comprises:

a first permanent magnet;

means for movement of said first magnet toward and away from said first position adjacent said first switch within said time totalizing means;

a second permanent magnet;

means for movement of said second magnet toward and away from said second position adjacent said second magnetic switch within said time totalizing means.

10. An improved water bottom contacting trawl door as recited in claim 9, wherein said first and second switching means are magnetic switches.

11. An improved water bottom contacting trawl door as recited in claim 10, wherein said means for communication of said flexible arm bending indication through said hollow tube to said first switching means comprises cable means connected between said attachment means and said first switching means.

12. A system for measurement of the total on-bottom time as recited in claim 11, in which said time totalizing means further comprises display means to convert said total time measurement to a visual output.

13. A system for measurement of the total on-bottom time recited in claim 12, wherein said bottom contacting means comprises:

a hollow tube mounted on said body section, having top and bottom ends thereon;

a flexible arm connected to said bottom end of said hollow tube and extending below said bottom edge portion of said body section so that said flexible arm will produce a bending indication when in moving contact with said water bottom; and means for communication of said flexible arm bending indication through said hollow tube to said switching means so that said bending indication from said bottom contacting means will activate said time totalizing means and that an absence of said indication will deactivate said time totalizing means.

14. A system for measurement of the total on-bottom time as recited in claim 13, wherein said flexible arm comprises:

spring means having inboard and outboard ends thereon with the inboard end connected to said bottom end of said hollow tube and the outboard end extending below said bottom edge portion of said body section;

a flexible arm tip connected to said outboard end of said spring means for contacting the bottom; and attachment means for connection of said communication means to said flexible arm tip for transmittal of the flexible arm bending indication through said hollow tube to said first switching means.

15. A system for measurement of the total on-bottom time as recited in claim 14, wherein said means for communication of said flexible arm bending indication through said hollow tube to said first switching means comprises cable means connected between said attachment means and said switching means so that said bending indication from said bottom contacting means will activate said time totalizing means and that an absence of said indication will deactivate said time totalizing means.

16. A system for measurement of the total on-bottom time as recited in claim 15, wherein said time totalizing means comprises:

clock means for generation of a time count when activated;

second switch means for activation of said clock means when a first magnet is moved toward a first position adjacent said second switch means;

means for deactivating said clock means and holding the count when said first magnet is moved away from said first position adjacent said second switch means; and third switch means for resetting said time count to zero when a second magnet is moved toward a second position adjacent said third switch means.

17. An improved water bottom contacting trawl door as recited in claim 16, wherein said first switching means connected between said bottom contacting means and said time totalizing means comprises:

a first permanent magnet;

means for movement of said first magnet toward and away from said first position adjacent said second switch within said time totalizing means;

a second permanent magnet;

means for movement of said second magnet toward and away from said second position adjacent said third magnetic switch within said time totalizing means.

18. A system for measurement of the total on-bottom time that an object with a body section having upper and lower portions thereof, being towed behind a boat is in actual contact with the water bottom, comprising:

means for mounting said time measurement system on said body section;

bottom contacting means mounted on said body section and extending below said bottom portion of said body section for indication of when said bottom portion of said body section is in proximate contact with said water bottom;

time totalizing means for measurement of time cumulation when activated and for holding said time cummulation when deactivated; and first switching means connected between said bottom contacting means and said time totalizing means so that a bottom contacting indication from said bottom contacting means will activate said time totalizing means and that an absence of said indication will deactivate said time totalizing means.

19. A method for measurement of the total on-bottom time that a boat towed object having a body section with upper and lower portions thereon, is in actual contact with the water bottom, comprising the steps of:

mounting said time measurement system on the lower portion of said body section;

contacting the bottom with a flexible arm connected to said bottom section and extending below said lower portion so that said flexible arm will produce a bending indication when in moving contact with said water bottom;

communicating said flexible arm bending indication through to a first switching means which will be activated by said flexible arm bending upon contacting the bottom and will be switched off by lack of bottom contact by said flexible arm;

totalizing time by means of starting a clock in response to activation of said first switching means;

holding an elapsed time total by means of stopping the clock in response to deactivation of said switching means; and displaying said elapsed time total for reading of total on-bottom time.

20. A method for measurement of the total on-bottom time as recited in claim 19, further comprising the steps of:

resetting the elapsed time total to zero by activation of a second switching means.

* * * * *